(12) United States Patent
Petcavich et al.

(10) Patent No.: US 8,113,210 B2
(45) Date of Patent: Feb. 14, 2012

(54) MEDICAL TUBE AND SYSTEM FOR LOCATING THE SAME IN A BODY USING PASSIVE INTEGRATED TRANSPONDERS

(75) Inventors: Robert J. Petcavich, Kirkland, WA (US); Murray Reicher, Rancho Santa Fe, CA (US)

(73) Assignee: Health Beacons, Inc., Kirkland, WA (US)

( * ) Notice: Subject to any disclaimer, the term of this patent is extended or adjusted under 35 U.S.C. 154(b) by 963 days.

(21) Appl. No.: 11/973,018

(22) Filed: Oct. 5, 2007

(65) Prior Publication Data

US 2008/0086046 A1    Apr. 10, 2008

Related U.S. Application Data

(60) Provisional application No. 60/849,825, filed on Oct. 6, 2006, provisional application No. 60/850,391, filed on Oct. 10, 2006.

(51) Int. Cl.
*A61B 19/00* (2006.01)
(52) U.S. Cl. ......................................... 128/899
(58) Field of Classification Search .................. 600/300, 600/587, 591, 595; 342/118; 606/1; 128/897, 128/898; 33/700; 73/1.79, 490
See application file for complete search history.

(56) References Cited

U.S. PATENT DOCUMENTS

| | | | |
|---|---|---|---|
| 4,809,713 A | 3/1989 | Grayzel | |
| 5,099,845 A | 3/1992 | Besz et al. | |
| 6,026,818 A | 2/2000 | Blair et al. | |
| 6,261,247 B1 * | 7/2001 | Ishikawa et al. | 600/587 |
| 6,496,717 B2 | 12/2002 | Cox et al. | |
| 6,698,433 B2 | 3/2004 | Krag | |
| 2003/0004411 A1 | 1/2003 | Govari et al. | |
| 2006/0117859 A1 * | 6/2006 | Liu et al. | 73/753 |
| 2006/0241396 A1 | 10/2006 | Fabian et al. | |

FOREIGN PATENT DOCUMENTS

EP    0 967 927 B1    4/2003

* cited by examiner

*Primary Examiner* — Tse Chen
*Assistant Examiner* — Elmer Chao
(74) *Attorney, Agent, or Firm* — Greer, Burns & Crain, Ltd.

(57) ABSTRACT

A medical tube has one or more permanent passive integrated transponders associated therewith that are capable of being located by a detection apparatus which senses the electromagnetic field strength gradient generated by each passive integrated transponder associated with the medical tube and indicates the value of the gradient to the user. In one embodiment, the passive integrated transponder is associated with the distal end of an endotracheal medical tube in a fixed orientation with an electromagnetic field pointing at a preferred angle of no more than 15 degrees to the longitudinal axis of the medical tube. The passive integrated transponder's static electromagnetic field is sensed by the detection apparatus and indicates the location of the distal end of the medical tube within a body.

20 Claims, 4 Drawing Sheets

MEDICAL TUBE AND SYSTEM FOR LOCATING THE SAME IN A BODY USING PASSIVE INTEGRATED TRANSPONDERS

CROSS-REFERENCE

This application claims the benefit of U.S. Provisional Applications No. 60/849,825, filed Oct. 6, 2006, and No. 60/850,391, filed Oct. 10, 2006.

FIELD OF THE INVENTION

This invention is generally directed to a medical tube, for example, an endotracheal tube or a nasogastric tube, and a detection system and method for ascertaining the location of the medical tube within a body, and, more specifically, to a medical tube capable of being located using a detection apparatus which senses a static electromagnetic field strength gradient generated by one or more passive integrated transponders associated with the medical tube.

BACKGROUND OF THE INVENTION

There are many instances in clinical medicine where detecting the location of a medical tube within a patient is important. For example, when positioning feeding tubes through the mouth or nose of a patient, it is essential that the end of the feeding tube pass into the patient's stomach, and that it does not "curl up" and remain in the esophagus. If the end of the feeding tube is not properly positioned within the stomach, aspiration of the feeding solution into the patient's lungs may occur. In addition to feeding tubes, a variety of other medical tubes require accurate positioning within a patient's body, including dilating tubes to widen an esophageal stricture, tubes for measuring pressure waves in the stomach and esophagus of a patient who is suspected of having esophageal motor disorders, Sengstaken-Blakemore tubes in the stomach and esophagus of a patient to control bleeding from varicose veins in the esophagus, colonic decompression tubes in the colon of a patient to assist in relieving distention of the colon by gas, urologic tubes in the bladder, ureter or kidney of a patient, and vascular tubes in the heart or pulmonary arteries of a patient.

Currently, the location of a medical tube within the body of a patient is routinely detected by the use of imaging equipment, such as a chest or abdominal X-ray. However, such a procedure requires transportation of the patient to an X-ray facility or, conversely, transportation of the X-ray equipment to the patient. This is both inconvenient and costly to the patient, and is particularly stressful in those instances where the patient repeatedly and inadvertently removes a medical tube, such as a feeding tube, thus requiring repeated reinsertion and X-rays.

Prior attempts at detecting the location of medical tubes within a patient have met with only limited success. For example, in U.S. Pat. No. 5,099,845 to Besz et al., a transmitter is located within a catheter, and an external receiver, tuned to the frequency of the transmitter, is used to detect the location of the catheter within the patient. This approach, however, requires either an external or internal power source to drive the transmitter. An external power source adds significant risk associated with shock or electrocution, and requires that electrical connections be made prior to positioning of the catheter within the patient. An internal power source, such as a battery, must be relatively small and can only provide power to the transmitter for a limited time. This precludes long-term detection of the catheter's location, and poses additional risks associated with placing a battery internally in a patient, such as the risk of battery leakage or rupture. In addition, the transmitter is relatively complex, and requires an active electronic circuit (either internal or external to the catheter), as well as the various wires and connections necessary for its proper function. Lastly, the signal produced by the transmitter is attenuated differently by different body tissues and bone. This attenuation requires adjustments in the transmitter's signal strength and frequency depending on the location of the catheter within the patient's body.

A further attempt at detecting the location of medical tubes within a patient is disclosed in U.S. Pat. No. 4,809,713 to Grayzel. There, an electrical cardiac-pacing catheter is held in place against the inner heart wall of a patient by the attraction between a small magnet located in the tip of the pacing catheter and a large magnet located on (e.g., sewn into) the patient's chest wall. An indexed, gimbaled, three-dimensional compass is used to determine the best location for the large magnet. The compass' operation relies upon the torque generated by the electromagnetic forces between the small magnet and the magnetized compass pointer in order to point the compass towards the small magnet. However, this compass will simultaneously try to orient itself to the earth's ambient electromagnetic field. Because of this, the forces between the small magnet and the magnetized compass pointer at distances greater than several centimeters are not strong enough to accurately orient the compass towards the small magnet. Furthermore, although the compass aids positioning of the large magnet, positioning of the small magnet, and hence the pacing catheter, still requires the use of imaging equipment, such as X-ray or ultrasound.

For the foregoing reasons, there is a need in the art for a medical tube, apparatus and method for detecting the location of the medical tube within the body of a patient which avoids the problems inherent in existing techniques. The medical tube, apparatus and method should provide for the detection of the medical tube at distances ranging from several centimeters to several decimeters, should not require the medical tube to have an internal or external power source, and should obviate the need to independently verify positioning of the medical tube with imaging equipment.

SUMMARY OF THE INVENTION

It is an object of the present invention to provide a medical tube, and a system and method for detecting the location of a medical tube within a body without the aid of imaging equipment, particularly X-ray.

A further object is to detect the location of a medical tube to which is attached a passive integrated transponder, and to thereby allow detection distances suitable for locating a wide variety of medical tubes at any location within a body.

The present invention satisfies these objectives by providing a medical tube, and a system, apparatus and method for detecting the location of one or more radio frequency, passive integrated transponders associated with a medical tube placed within a body.

In one aspect of this invention, a medical tube is disclosed having at least one permanent passive integrated transponder associated therewith. In one embodiment, the medical tube comprises a tube or device, for example, an endotracheal or nasogastric tube, suitable for insertion into a body and at least one permanent passive integrated transponder associated with the medical tube, wherein the permanent passive integrated transponder is preferably associated with the medical tube in a manner such that it is oriented at an angle that is no greater than 15 degrees to the long axis of the medical tube.

In another embodiment, the medical tube is a Sengstaken-Blakemore tube comprising an esophageal balloon, a gastric balloon and a permanent passive integrated transponder, wherein the permanent passive integrated transponder is associated with the tube at a location between the esophageal balloon and gastric balloon.

In still a further embodiment, the medical tube comprises a tube or device suitable for insertion into a body and a permanent passive integrated transponder associated with the medical tube, the medical tube having a proximal end and a distal end. The permanent passive integrated transponder generates an electromagnetic field of sufficient strength to permit detection by a radio frequency scanner or detection apparatus that emits and receives signals from the transponder and has a visual display and/or an audible tone generator. The passive integrated transponder is associated with the distal end of the medical tube in a fixed orientation with a electromagnetic field oriented at an angle that is no greater than 15 degrees to a longitudinal axis of the medical tube such that the passive integrated transponder's static electromagnetic field is sensed by the scanning apparatus which detects and indicates, visually and/or aurally, the orientation and location of the distal end of the medical tube within the body.

By sensing the static electromagnetic field strength of the passive integrated transponder associated with the medical tube, the present invention obviates the need for imaging equipment, such as X-ray, to verify positioning of the medical tube.

In one preferred embodiment, the visual display comprises a light emitting diode bar array or LCD screen.

In another preferred embodiment, the apparatus further comprises a tone generator for receiving a field magnitude signal from the transponder and for providing a tone signal proportional to the electromagnetic field magnitude, and a speaker for audibly annunciating the tone signal.

These and other features of the present invention will be become apparent to those of reasonable skill in the art from the following detailed description, as considered in conjunction with the accompanying drawings.

DETAILED DESCRIPTION OF PREFERRED EMBODIMENTS OF THE INVENTION

Figure 1:
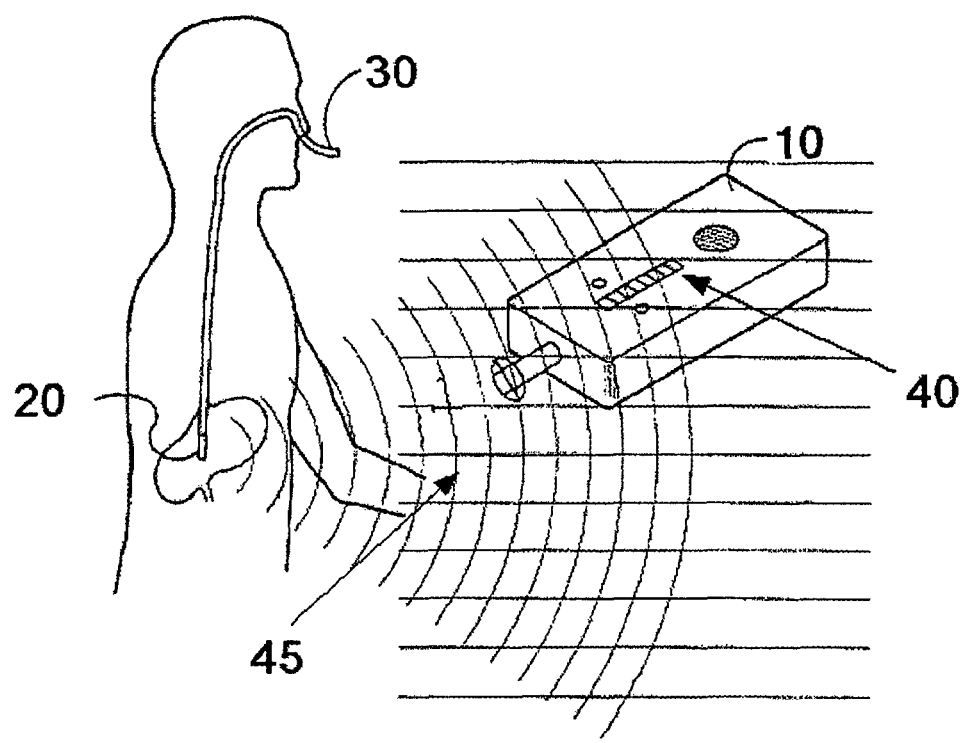
FIG. 1 illustrates a system provided in accordance with the invention for detecting the location of the distal end of a nasogastric tube positioned within a body using the detection or scanning apparatus of FIG. 2.

The following is a detailed description of certain embodiments of the invention presently contemplated by the inventors to be the best mode of carrying out their invention.

The invention provides a medical tube, and a system, apparatus and method for detecting the location of a medical tube within a body. As used herein, the term "medical tube" means any type of tube or device which may be inserted into a body, including (but not limited to) catheters, guide wires, and medical instruments. For example, catheters include such items as feeding tubes, urinary catheters, guide wires and dilating catheters, as well as nasogastric tubes, endotracheal tubes, stomach pump tubes, wound drain tubes, rectal tubes, vascular tubes, Sengstaken-Blakemore tubes, colonic decompression tubes, pH catheters, motility catheters, and urological tubes. Guide wires are often used to guide or place dilators and other medical tubes. Medical instruments include endoscopes and colonoscopes and are encompassed within the term "medical tube."

The present invention detects the location of a medical tube by sensing the static electromagnetic field strength gradient produced by at least one permanent passive integrated transponder ("PIT") associated with the medical tube. As used herein, the term "associated with" means permanently fixed, removably attached, or in close proximity to, the medical tube. The PIT/element or elements may be on the interior of the tube or the exterior of the tube or may be molded or imbedded in the wall of the tube. In one embodiment, such as a feeding tube, the passive integrated transponder (PIT) is associated with the distal end of the medical tube. In another embodiment, such as a Sengstaken-Blakemore tube, the passive integrated transponder is associated with the medical tube at a location above the gastric balloon. In a further embodiment, for example an endotrachael tube, a plurality of PIT elements may be associated with the tube at longitudinally spaced locations along the tube, as well as at the distal end of the tube. Preferably, the passive integrated transponder is a small, cylindrical, rotatably attached, element containing a transponder antenna and an information bearing microchip; the cylinder ranging in diameter from about 1 to 6 millimeters (mm) with 2 to 4 mm being preferred, and in length from about 2 to 30 millimeters with 8 to 15 mm being preferred. The transponder is preferably oriented at an angle of no more than 15 degrees to the longitudinal axis of the tube so that the poles of the transponder's magnetic field are more easily detected.

Since the passive integrated transponder is permanent and emits a signal only when interrogated by a reader, it requires no power source. The transponder maintains its electromagnetic field indefinitely, which allows long-term positioning and detection of medical tubes without the disadvantages associated with an internal or external power source. In particular, by avoiding the use of a power source, the undesirable electrical connections necessary for the use of a power source are avoided. Thus, there is no risk of shock to (or possible electrocution of) the patient. Furthermore, the passive integrated transponder's static electromagnetic field passes unattenuated through tissue and bone. This property allows practice of the present invention to detect a medical tube at any location within a body.

The passive integrated transponder, and hence the medical tube, is detected and read using a grid dip oscillator detection apparatus. The detection apparatus is an active, electronic instrument, and can detect the relatively small electromagnetic field strength gradient produced by the passive integrated transponder at distances ranging from several centimeters to several decimeters, and preferably from about 0.5 centimeters to about 10 centimeters. It also indicates the value of the gradient, thus allowing the user to accurately determine the location of the passive integrated transponder, and hence the medical tube. In a preferred embodiment, the grid dip oscillator is embodied in a small, hand-held scanner operating at a radio frequency of 134.2 kHz and powered by a self-contained 9 volt battery, and provides a read-out indicative of the value of the transponder field strength. By manipulating the passive integrated transponder until detection, the location of the medical tube can be verified. Such manipulation of the passive integrated transponder can be accomplished either by means of an attached guide wire or by rotating the medical tube itself.

Due to the sensitivity of the grid dip detection apparatus to the transponder's field strength gradient, additional imaging equipment is not necessary to detect the location of the medical tube. Accordingly, the present invention is suitable for use in environments which lack such equipment. For example, ambulances and nursing homes rarely have X-ray equipment on-site, and the apparatus and method of the invention are particularly suited for use in such facilities and situations. A major advantage of the invention is that the method and apparatus can routinely be used at a bedside, for easy efficient and inexpensive ongoing bedside monitoring without radiation.

Referring to FIG. 1, a nasogastric tube 30 having a permanent passive integrated transponder 20 at or adjacent its distal end is illustrated inserted in a body. In a preferred embodiment, a grid dip meter sensor 10 measures the amount of electromagnetic energy from the passive integrated transponder 20 attached to the medical tube 30. A grid dip meter is an oscillator whose output energy changes in the vicinity of a circuit which is in resonance with the frequency the oscillator generates, somewhat similar to an acoustic tone becoming louder when generated in the vicinity of a resonant cavity. When the detection apparatus is brought in proximity to the passive integrated transponder, the sensed value of the transponders electromagnetic field is displayed by a reading device 40, integrated with the sensor 10. In the preferred embodiment the PIT tag attached to the medical tube operates in a frequency range of 1 KHz to 5.4 GHz with 120 to 135 KHz being the preferred range.

Figure 2:
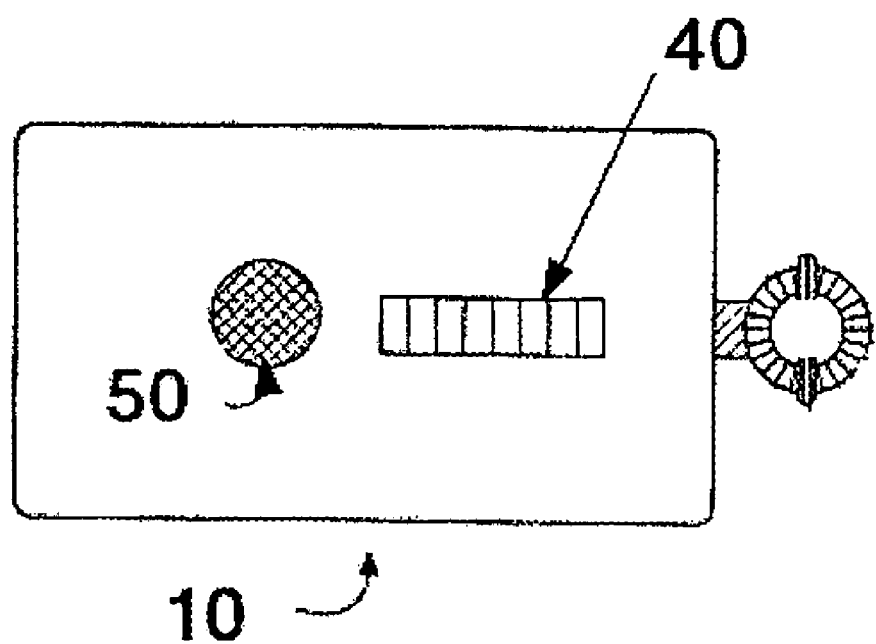
FIG. 2 illustrates an embodiment of a grid dip meter detection apparatus provided in accordance with the invention.

Referring to FIG. 2, the reading device 40 visually displays a representation of the passive integrated transponder's electromagnetic field strength gradient. Such a representation can be made with a light-emitting diode bar array or a liquid crystal display. In addition, a speaker 50 may optionally but preferably be employed. A tone generator receives the electromagnetic signal and provides a tone signal to the speaker. The tone signal is proportional to the magnitude of the electromagnetic signal of the PIT device. The sound projected by the speaker may change in volume or pitch corresponding to the magnitude of the PIT signal. Such a visual display 40 and/or speaker 50 allows the user to move or sweep the detection apparatus over the patient's body and to quickly determine the nearest external point to the location of the internal passive integrated transponder 20 associated with the medical tube.

Figure 3:
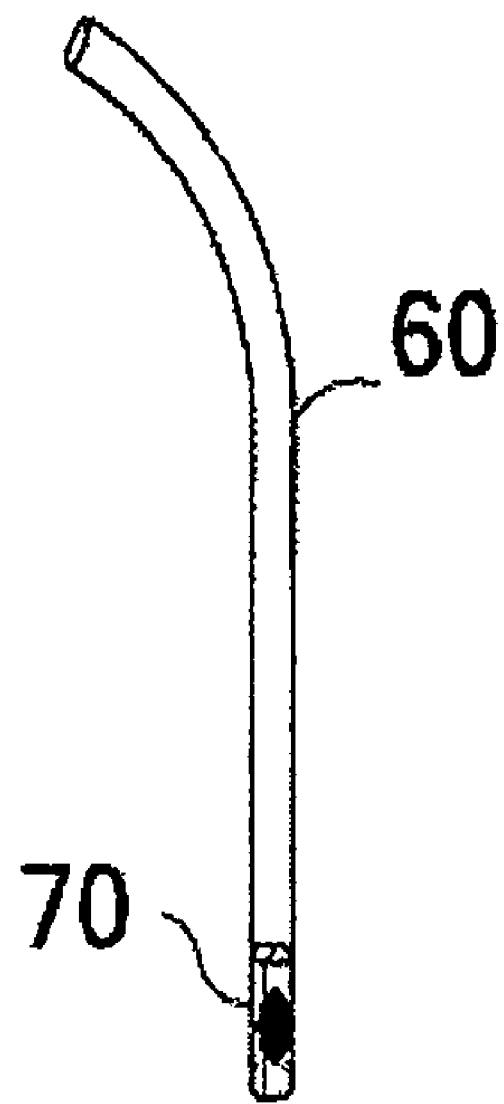
FIG. 3 illustrates an embodiment of the invention of a medical tube having a passive integrated transponder associated with its distal end.

Referring to FIG. 3 in a further embodiment with respect to a feeding tube 60, a passive integrated transponder 70 may be incorporated into the tip of the tube 60. The small size of the passive integrated transponder helps the tube be passed and advanced down the trachea and esophagus and into the stomach. In this embodiment, the size of the passive integrated transponder should not exceed about 15 mm in diameter, with 6 to 12 being preferred, so that it can be passed into the stomach via either the nose or mouth. Once in place, the location of the passive integrated transponder, and thus the end of the feeding tube, can be determined by the reading apparatus of the invention (FIG. 2).

Figure 4:
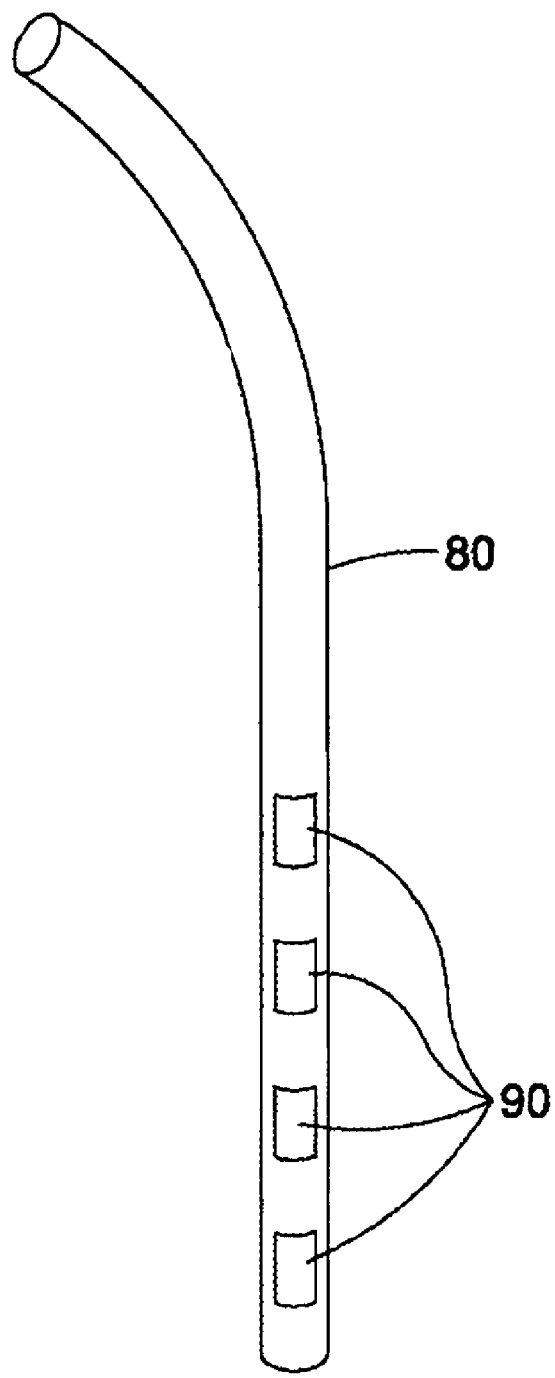
FIG. 4 illustrates an embodiment of the invention of a medical tube having a plurality of passive integrated transponders spaced longitudinally along the tube.

Referring to FIG. 4, in a further embodiment of the invention, an endotrachael tube 80 is provided with a plurality of passive integrated transponders 90 spaced from one another along the longitudinal axis of the tube. In this example, multiple PIT elements 90 are used to provide a range of detection sites to identify and bracket a specific locale in the trachea and/or to provide for more precise location of the tube and/or as a safe-guard in the event the magnetic field of one of the PIT elements is weak, disrupted or undetectable.

As the sensor 10 is scanned over the length of a transponder 20, the transponder returns to the sensor a peak signal at each end (the magnetic poles of the electromagnetic field) of the transponder and a relatively minor signal when the scanner is aligned with the mid-portion of the transponder. The peak signals thus bracket the location of each transponder in the body, e.g., in the trachea.

The method, apparatus and system of the invention can thus be used to detect the location of a wide variety of medical tubes within a body including for example, a nasogastric tube, endotracheal tube, stomach pump tube, wound drain tube, rectal tube, vascular tube, Sengstaken-Blakemore tube, colonic decompression tube and urological tube.

Similarly, for several procedures in gastroenterology and other specialties, it is necessary to pass a guide wire into an organ. Once the guide wire is in place (usually with the assistance of an endoscope), another tube is passed over the guide wire. An example is esophageal stricture management. In this instance, there is a narrowing of the esophagus, and patients complain of trouble swallowing (dysphagia). A common technique used to dilate the stricture is to place a wire through the stricture and into the stomach, and then pass progressively larger dilators over the wire. The wire thus acts like a monorail or guide to keep the tip of the larger dilator catheter in the lumen. This reduces the chance of causing a perforation or hole in the esophagus. To ensure that the tip of the guide wire is in the stomach, x-ray verification is normally utilized.

In practice of this invention, the location of such a guide wire may be confirmed by placing a passive integrated transponder at or near the end of the guide wire, or by placing a number of transponders along the length of the wire. With regard to such esophageal stricture guide wires, the wire must be relatively stiff. The present invention permits a physician to confirm that the tip of the guide wire remains in the stomach after the use of each progressively larger dilator.

This invention also permits the use of a guide wire having a spring tip/passive integrated transponder end without the need for endoscope placement. Rather, the guide wire may be passed directly into the stomach, and its location determined by the system of this invention. The size limitations associated with the use of an endoscope (i.e., the 2.5-3.5 mm diameter channel) can thus be avoided, and larger guide wires or tubes bearing passive integrated transponders can be employed. For example, a flexible tube of about 8 mm in diameter and bearing one or more passive integrated transponders can readily be passed into the stomach, and larger dilators passed over the flexible tube. In this embodiment, the need for a spring is obviated due to the use of the larger diameter flexible tube rather than the guide wire.

As a medical tube is inserted into a patient, the location of the passive integrated transponder can be sensed by moving the detection apparatus over the surface of the body and watching the visual display. As the sensor approaches the passive integrated transponder inside the body, the display will indicate a greater magnitude, by increasing the height of the display bar graph 40, and/or by increasing the volume or pitch of the sound projected by the speaker 50. Also, after initial tube positioning, the location of the passive integrated transponder can be similarly verified at any time.

Although the present invention has been described in detail, with reference to certain preferred embodiments, other embodiments are possible. For example, one skilled in this art would understand that the invention may be implemented with analog, mixed-mode, or digital elements, and with either discrete components or integrated circuits, or both. Furthermore, the following specific examples are offered by way of illustration, not limitation.

Example 1

Detection of a Feeding Tube

The feeding tube 30 shown in FIG. 1 is inserted into a patient's nose, down the esophagus and into the stomach. The detection apparatus (10) is employed to sense the passive integrated transponder's field strength. As the detection apparatus 10 is scanned about the patient's body, greater and lesser electromagnetic field gradients 45 are indicated. The closer to the PIT tag is to the grid dip oscillator detection device the greater is the reader signal. The feeding tube 30 is located by moving the detection apparatus until the greatest magnitude is indicated by the detection apparatus visual display and/or speaker sound volume or pitch.

Example 2

Detection of an Endotracheal Tube with Multiple PIT Tags

The endotrachael tube 80 shown in FIG. 4 is inserted into the patient's mouth and into the airway to the lungs. The multiple PIT tags (90) are used in order to allow a range of detection sites so as to bracket the precise location in the patient. This method allows more precise detection of the tube in the event the electromagnetic field of any one tag is disrupted or undetectable.

From the foregoing, it will be appreciated that, although specific embodiments of this invention have been described herein for purposes of illustration, various modifications may be made without deviating from the scope of the invention as defined by the appended claims.

What is claimed is:

1. A medical device comprising:
 a medical tube configured for positioning in a body and defining a longitudinal axis;
 a passive integrated transponder on said tube, said transponder configured for generating an electromagnetic signal at a designated frequency in a frequency range of 120 kHz to 135 kHz; and
 a handheld reading device tuned to said designated frequency and including a grid dip oscillator and processing means configured for determining each end of said transponder by sensing magnetic poles of the electromagnetic signal generated by said transponder at said designated frequency when said reading device is physically moved over said transponder on said medical tube while said medical tube is in the body and determining a location of said transponder based on said locations of the magnetic poles sensed by said reading device, said reading device configured for providing at least one of a visual signal and an audio signal proportional to a magnitude of the electromagnetic signal sensed by said reading device for determining the locations of each end and a mid-portion of said transponder.

2. The medical device as set forth in claim 1 wherein said tube has a proximal end and a distal end and said transponder is on the distal end of said tube.

3. The medical device as set forth in claim 1 including a plurality of passive integrated transponders on said tube and spaced longitudinally along said tube.

4. The medical device as set forth in claim 1 wherein a front surface of said transponder is oriented at an angle of no more than 15 degrees relative to the longitudinal axis of said tube.

5. The medical device as set forth in claim 4, said transponder is configured for enabling ascertainment of the orientation of said tube in the body.

6. The medical device as set forth in claim 2 wherein said tube comprises a gastric tube.

7. The medical device as set forth in claim 3 wherein said tube comprises an endotracheal tube.

8. A medical apparatus comprising:
 a medical tube configured for positioning in a body and defining a longitudinal axis;
 at least one passive integrated transponder on said tube and configured for generating a radio frequency signal at a designated frequency in a frequency range of 120 kHz to 135 kHz;
 a handheld grid dip oscillating scanner and processing means tuned to said designated frequency and configured for sensing a peak signal of said radio frequency signal at said designated frequency at each end of said at least one transponder and a mid-portion signal between each of said peak signals indicating a mid-portion of said at least one transponder when said scanner is physically moved over a length of said transponder on said medical tube while said medical tube is in the body, said scanner configured to provide at least one of a visual signal and an audio signal proportional to a magnitude of the radio frequency signal sensed by said scanner for determining locations of each end and said mid-portion of said at least one transponder and thereby a location of at least a portion of said medical tube in the body.

9. The medical apparatus as set forth in claim 8 wherein said tube has a proximal end and a distal end and said at least one transponder is on the distal end of said tube, said scanner configured for determining a location of the distal end of said tube.

10. The medical apparatus as set forth in claim 9 wherein said tube comprises a gastric tube.

11. The medical apparatus as set forth in claim 8 including a plurality of passive integrated transponders on said tube and spaced longitudinally along said tube.

12. The medical apparatus as set forth in claim 11 wherein said tube comprises an endotracheal tube and said scanner determines a location of said tube within the trachea.

13. The medical apparatus as set forth in claim 8 wherein a front surface of said at least one transponder is oriented at an angle of no more than 15 degrees relative to the longitudinal axis of said tube to aid in determining by the scanner of both the location and the orientation of said tube in the body.

14. A system for detecting a medical tube within a body comprising:
 a medical tube configured for insertion into a body and a plurality of permanent passive integrated transponders on the medical tube, the permanent passive integrated transponders each configured for generating a static electromagnetic field at a designated frequency in a frequency range of 120 kHz to 135 kHz to permit detection of the electromagnetic field when the medical tube is inserted into the body, and
 a handheld detection apparatus tuned to said designated frequency and configured for physically scanning the body, said detection apparatus comprising a grid dip oscillator configured for sensing electromagnetic field strength at said designated frequency and processing means operatively associated with the grid dip oscillator for indicating electromagnetic field strength signals received by the grid dip oscillator, wherein said detection apparatus is configured to be physically scanned over the body and the processing means is configured for sensing a peak signal of the electromagnetic field strength signals at each end of at least one of said plurality of transponders while said medical tube is in the body for determining a location and orientation of said at least one transponder and thus a location and orientation of the medical tube within the body.

15. The system as set forth in claim 14 wherein the medical tube is selected from the group comprising catheters and medical instruments.

16. The system as set forth in claim 14 wherein the medical tube is a catheter selected from the group consisting of a nasogastric tube, endotracheal tube, stomach pump tube, wound drain tube, rectal tube, vascular tube, Sengstaken-Blakemore tube, colonic decompression tube and urological tube.

17. The system as set forth in claim 14 wherein the medical tube has a proximal end and a distal end and said at least one transponder is associated with the distal end of the tube.

18. The system as set forth in claim 14 wherein said plurality of permanent passive integrated transponders on said tube are spaced longitudinally along said tube.

19. The system as set forth in claim 14 wherein the medical tube is a feeding tube having a proximal end and a distal end with a tip and wherein at least one of said plurality of passive integrated transponders is on a tip of the tube.

20. A method of locating a medical tube within a body comprising the steps of:

affixing a permanent passive integrated transponder configured for generating an electromagnetic field at a designated frequency in a frequency range of 120 kHz to 135 kHz to a medical tube prior to insertion of the tube into the body; and inserting said medical tube into the body;

physically scanning the body with a handheld sensor including a grid dip oscillator and processing means tuned to said designated frequency and sensing a peak signal of the transponder's electromagnetic field at each end of said transponder while said medical tube is in the body; and providing at least one of a visual signal and an audio signal proportional to a magnitude of the electromagnetic field sensed by said sensor and determining a location of the transponder while the transponder is on the medical tube based on said peak signal sensed at each end of said transponder, and thus, determining the location of at least a portion of the medical tube within the body.

* * * * *